United States Patent [19]

Cragoe, Jr. et al.

[11] 4,221,790

[45] Sep. 9, 1980

[54] SUBSTITUTED 2,2-DIOXO-1,2,3-BENZOXATHIAZINES

[75] Inventors: Edward J. Cragoe, Jr.; Robert L. Smith, both of Lansdale; Gerald E. Stokker, Gwynedd Valley, all of Pa.

[73] Assignee: Merck & Co., Inc., Rahway, N.J.

[21] Appl. No.: 30,409

[22] Filed: Apr. 16, 1979

Related U.S. Application Data

[62] Division of Ser. No. 864,185, Dec. 27, 1977, Pat. No. 4,166,177.

[51] Int. Cl.$^2$ ............................................. A61K 31/54
[52] U.S. Cl. ................................................... 424/246
[58] Field of Search ......................................... 424/246

[56] References Cited

U.S. PATENT DOCUMENTS 3,317,523   5/1967   Wright ................................. 424/246

*Primary Examiner*—Stanley J. Friedman
*Attorney, Agent, or Firm*—Raymond M. Speer; Mario A. Monaco

[57] ABSTRACT

The invention relates to novel 2,2-dioxo-1,2,3-benzoxathiazines substituted in the benzene nucleus, as well as the 3,4-dihydro analogs thereof, useful as anti-inflammatory, antipyretic, analgesic agents.

10 Claims, No Drawings

SUBSTITUTED 2,2-DIOXO-1,2,3-BENZOXATHIAZINES

This is a division of application Ser. No. 864,185, filed Dec. 27, 1977, now U.S. Pat. No. 4,166,177.

BACKGROUND OF THE INVENTION

1. Field of the Invention

The present invention is concerned with novel 2,2-dioxo-1,2,3-benzoxathiazenes substituted in the benzene nucleus, as well as the 3,4-dihydro analogs thereof. The present invention is also concerned with methods of preparing these novel compounds.

The present invention is further concerned with a method of treating a condition exhibiting at least one of the symptoms of pain, fever and inflammation which comprises the administration to a patient in need of such treatment a therapeutically effective amount of a novel compound of the present invention. The present invention is also further concerned with pharmaceutical compositions comprising a non-toxic, pharmaceutically acceptable carrier and as an active ingredient, at least one of the novel compounds of the present invention.

2. Description of the Prior Art

Heretofore, considerable research has been devoted to the discovery and development of anti-inflammatory drugs. Many of these have been steroids of the 11-oxygenated pregnane series, for example dexamethasone, while others have been non-steroidal, for example indomethacin. While many of these compounds have been found to be effective anti-inflammatory agents, the search has continued for new compounds of higher potency and higher therapeutic index, that is, having lower toxicity and fewer undersirable side effects. Among such new compounds are the aminomethylphenol compounds described in U.S. Pat. Nos. 3,928,624, 3,979,367 and 4,044,153. However, such compounds do not suggest the novel substituted 2,2-dioxo-1,2,3-benzoxathiazenes of the present invention.

SUMMARY OF THE INVENTION

The present invention relates to novel substituted 2,2-dioxo-1,2,3-benzoxathiazine compounds having the following structural formula:

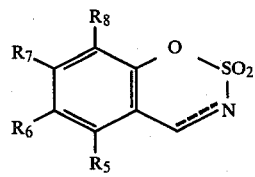

(I)

wherein $R_5$ is hydrogen; $C_{1-3}$ alkyl, for example, methyl or propyl; halogen, for example, fluoro or chloro; or $C_{1-3}$ alkoxy, for example, ethoxy;

$R_6$ is hydrogen; $C_{1-5}$ straight or branched chain alkyl, for example, ethyl, iso-propyl, or tert-butyl; or halogen, for example, fluoro or iodo;

$R_7$ is hydrogen; $C_{1-5}$ alkyl, for example, n-butyl or n-pentyl; $C_{1-5}$ alkoxy, for example, propoxy or butoxy; or halogen, for example, bromo or chloro;

$R_8$ is hydrogen; halogen, for example, bromo, chloro, or iodo; trifluoromethyl; or $C_{1-3}$ alkylthio, for example, methylthio; and the dashed line between the 3- and 4- positions describes the unsaturation as alternative, that is, that the 3,4-dihydro compounds are also included. Thus, the novel compounds of the present invention may also be represented by the following two structural formulas:

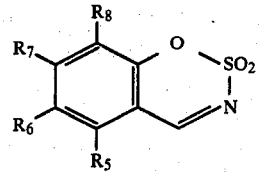 and 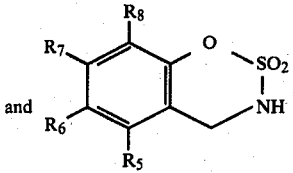

(II) (III)

wherein $R_5$, $R_6$, $R_7$, and $R_8$ are as previously defined.

A more preferred aspect of this invention consists of those compounds of formulas I wherein:

$R_5$ is hydrogen, or $C_{1-3}$ alkoxy;

$R_6$ is hydrogen, halogen, or $C_{3-5}$ branched chain alkyl;

$R_7$ is hydrogen or $C_{1-3}$ alkoxy; and $R_8$ is hydrogen, halogen, trifluoromethyl or $C_{1-3}$ alkylthio.

A most preferred aspect of this invention consists of those compounds of formula I wherein:

$R_5$ and $R_7$ are hydrogen or methoxy;

$R_6$ is hydrogen, chloro, bromo, iodo, or $C_{3-5}$ branched chain alkyl; and $R_8$ is hydrogen, chloro, bromo, iodo, trifluoromethyl or methylthio.

Preferred specific compounds of the present invention are, among others, the following:

2,2-dioxo-6-(1,1-dimethylethyl)-8-iodo-1,2,3-benzoxathiazine;

2,2-dioxo-6-(1,1-dimethylethyl)-8-bromo-1,2,3-benzoxathiazine;

2,2-dioxo-6-(1,1-dimethylethyl)-8-chloro-1,2,3-benzoxathiazine;

2,2-dioxo-1,2,3-benzoxathiazine;

2,2-dioxo-6-(1,1-dimethylethyl)-8-trifluoromethyl-1,2,3-benzoxathiazine;

2,2-dioxo-5,7-dimethoxy-6,8-dichloro-1,2,3-benzoxathiazine;

2,2-dioxo-6-(1,1-dimethylethyl)-8-methylthio-1,2,3-benzoxathiazine;

2,2-dioxo-3,4-dihydro-6-(1,1-dimethylethyl)-8-iodo-1,2,3-benzoxathiazine;

2,2-dioxo-3,4-dihydro-6-(1,1-dimethylethyl)-8-bromo-1,2,3-benzoxathiazine;

2,2-dioxo-3,4-dihydro-6-(1,1-dimethylethyl)-8-chloro-1,2,3-benzoxathiazine;

2,2-dioxo-3,4-dihydro-1,2,3-benzoxathiazine;

2,2-dioxo-3,4-dihydro-6-(1,1-dimethylethyl)-8-trifluoromethyl-1,2,3-benzoxathiazine;

2,2-dioxo-3,4-dihydro-5,7-dimethoxy-6,8-dichloro-1,2,3-benzoxathiazine;

2,2-dioxo-3,4-dihydro-6-(1,1-dimethylethyl)-8-methylthio-1,2,3-benzoxathiazine.

The present invention also relates to a method of treating inflammation in patients using a compound of Formula I, particularly a preferred compound, as the active ingredient.

It has been found that the compounds of Formula I have anti-inflammatory activity as shown by inhibition of inflammation in the topical mouse ear inflammation assay.

The compounds of the present invention can be used to treat inflammation by reducing inflammation and relieving pain in such diseases as rheumatoid arthritis, osteoarthritis, gout, infectious arthritis, and rheumatic fever.

The compounds of Formula I also have anti-pyretic and analgesic activity and would be administered and used in the same manner and in the same dosage ranges as if they were being used to treat inflammation as described hereafter.

For these purposes the compounds of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection, intraarticular, or infusion techniques. In addition to the treatment of warm-blooded animals such as mice, rats, horses, dogs, cats, guinea pigs, rabbits, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweeting agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatine or acacia, and lubricating agents, for example magnesium stearate, steric acid or talc. The tablets may be uncoated or they may be coated by known techniques to delay disintegration and adsorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, the example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol mono-oleate, or condensation products of ethylene oxide with partial esters derived from fatty acids and hexitol anhydrides, for example polyoxyethylene sorbitan mono-oleate. The said aqueous suspensions may also contain one or more preservatives, for example ethyl, or n-propyl, p-hydroxy benzoate, one or more coloring agents, one or more flavoring agents, and one or more sweetening agents such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the present invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occuring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

In a particularly preferred aspect of the present invention, the compounds of Formula I are used as topical anti-inflammatory agents and are particularly effective in topical treatment of dermatological disorders and like conditions, such as dermatitis (actinic, atopic, contact, eczematoid, seborrheic and stasis), dermatitis herpetiformis, lichen planus, neurodermatitis, intertrigo, lichen simplex chronicus, pruritus and psoriasis, as well as for topical treatment of inflammations of the respiratory and intestinal mucosa such as allergic rhinitis, bronchitis, bronchial asthma bronchiectasis, colitis and the like. The compounds of Formula I are ordinarily administered in the form of a pharmaceutical composition comprising the active compound in combination with a pharmacologically acceptable carrier adapted for topical administration. These topical pharmaceutical compositions may be in the form of a cream, ointment, gel or aerosol formulation adapted for application to the skin for treatment of dermatoses; or it may be in the form of a solution, suspension or aerosol adapted for topical spray application to respiratory passages for treatment of nasal allergies, bronchial inflammations, and the like; or in the form of suppositories or enclosed in enteric capsules for treatment of intestinal inflammations. For treatment of dermatological disorders, these topical pharmaceutical compositions containing the compounds of Formula I ordinarily include about 0.01% to 15%, preferably about 5% of the active compound, in admixture with 95% of gel vehicle comprising water, at least one organic solvent, and at least one thickening agent. The water ordinarily constitutes from about 8% to 18% of the gel vehicle, preferably about 13%. The organic solvent ordinarily constitutes about 60% to 90% of the gel vehicle. Representative solvents are ethyl alcohol, isopropyl alcohol, propylene glycol, glycerine, 2-octyl dodecanol and methyl pyrrolidine, and preferably isopropyl alcohol; propylene glycol mixtures at a ratio of 0.5 to 0.6 parts isopropyl alcohol to 1.0 parts propylene glycol. The solubility of the compounds of Formula I in the solvent system selected should be such as to obtain maximum partitioning of the active compound from the vehicle to the skin. The thickening agent, preferably hydroxyethyl cellulose, hydroxypropyl cellulose, and the like, ordinarily constitutes from 0.5 to 4.0% of the gel vehicle. Optionally, a stabilizing agent such as disodium edetate, sodium citrate, dipotassium edetate, citric acid, and the like, in the proportion of about 0.02% to 0.1% of the gel vehicle may be employed, if desired.

A preferred topical pharmaceutical composition is prepared as follows: About 2.60 g. of hydroxypropyl cellulose is added to a solution of 0.05 g. of disodium edetate in 13.00 g. purified water while agitating the mixture and maintaining the temperature at about 60° C., and the agitation is continued until the hydroxypropyl cellulose is completely dispersed and wetted. To the resulting dispersed mixture is added, with agitation, a solution containing 5.0 g. of, for example, 2,2-dioxo-3,4-dihydro-6-t-butyl-8-chloro-1,2,3-benzoxathiazine dispersed in a mixture of 30.00 g. of anhydrous isopropyl alcohol and 49.35 g. of propylene glycol. The resulting gel mixture is stirred vigorously at room temperature for a period of approximately 15 minutes thereby forming a pharmaceutical composition adapted for the treatment of topical inflammatory conditions.

The daily dosage of the compounds of Formula I may be varied over a wide range from 50 to 2,000 mg. Preferably, the compound of Formula I, either by itself, or with a carrier in pharmaceutical composition, is administered in subdivided doses containing 5, 10, 25, 50, 100, 150, 250 and 500 mg. of the active ingredient for the symptomatic adjustment of the dosage to the patient to be treated. An effective amount of the drug is ordinarily supplied at a dosage level of from about 1 mg. to about 50 mg./kg. of body weight. Preferably the range is from about 1 mg. to 7 mg./kg. of body weight.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The substituted 2,2-dioxo-1,2,3-benzoxathiazines of this invention of Formula II:

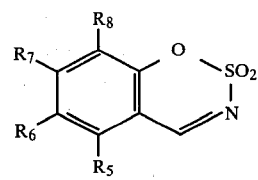

(II)

wherein $R_5$, $R_6$, $R_7$, and $R_8$ are as previously defined, can be prepared by the following synthetic method. A substituted salicylaldehyde of the formula.

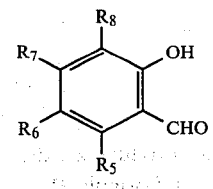

(IV)

wherein $R_5$, $R_6$, $R_7$, and $R_8$ are as previously defined, is made to react with sulfamoyl chloride in the presence of a suitable base to give the compounds of Formula II. A more detailed description of this method follows.

A substituted salicylaldehyde of formula IV wherein $R_5$, $R_6$, $R_7$, and $R_8$ are as previously defined, is made to react with sulfamoyl chloride in the presence of a suitable base such as triethylamine, pyridine, collidine and the like, preferably triethylamine, in an inert solvent such as methylene chloride, chloroform, tetrahydrofuran and the like, preferably methylene chloride, at a temperature ranging from 0° C. to the reflux temperature of the solvent, preferably at or about room temperature, for a period of 2 to 10 days, preferably 3 to 5 days to give, after work-up with aqueous acid, the product 2,2-dioxo-1,2,3-benzoxathiazine of formula II. The reaction of this synthetic method may be represented as follows:

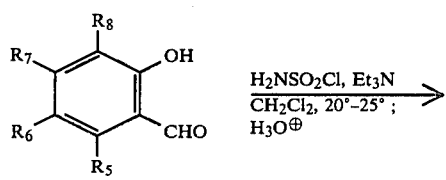

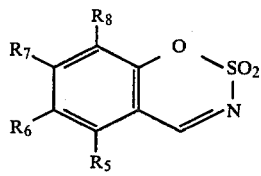

The substituted 2,2-dioxo-3,4-dihydro-1,2,3-benzoxathiazines of this invention of Formula III.

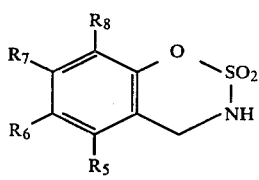

wherein $R_5$, $R_6$, $R_7$ and $R_8$ are as previously defined, can be prepared by the following synthetic method. A substituted 2,2-dioxo-1,2,3-benzoxathiazine of Formula II wherein $R_5$, $R_6$, $R_7$, and $R_8$ are as previously defined, is reduced with an alkalai metal borohydride reagent to give the compounds of Formula III. A more detailed description of this method follows.

A substituted 2,2-dioxo-1,2,3-benzoxathiazine of Formula II wherein $R_5$, $R_6$, $R_7$, and $R_8$ are as previously defined, is treated with a suitable alkalai metal borohydride reagent, preferably sodium or potassium borohydride, in a suitable solvent, preferably methanol, ethanol and the like, at a temperature ranging from 0° to 40° C., preferably 20° to 25° C., for a period of 6 to 24 hours, preferably 12 to 20 hours, to afford, after the usual aqueous work-up, the product 2,2-dioxo-3,4-dihydro-1,2,3-benzoxathiazine of Formula III. The reaction of this synthetic method may be represented as follows:

[Reaction scheme (II) → (III) with NaBH₄, CH₃OH, 20°–25° C.; H₃O⊕]

In addition, a particular group of 3,4-dihydro compounds of the present invention of the following formula:

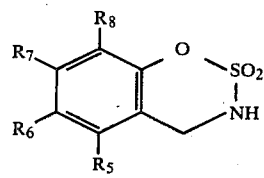

wherein $R_5$ is hydrogen, $C_{1-3}$ alkyl, chloro, or $C_{1-3}$ alkoxy $R_6$ is hydrogen, chloro or $C_{1-5}$ straight or branched chain alkyl; $R_7$ is hydrogen, chloro, $C_{1-5}$ alkyl, or $C_{1-5}$ alkoxy; and $R_8$ is hydrogen or chloro, can be prepared by catalytic hydrogenation of the corresponding 2,2-dioxo-1,2,3-benzoxathiazines of Formula VI.

[Formula (VI) structure]

wherein $R_5$, $R_6$, $R_7$ and $R_8$ are as defined above for Formula V.

The above process involves hydrogenation of a substituted 2,2-dioxo-1,2,3-benzoxathiazine of Formula VI wherein $R_5$, $R_6$, $R_7$, and $R_8$ are as previously defined, in a suitable solvent, preferably acetic acid and the like, in the presence of a suitable hydrogenation catalyst, preferably platinum (IV) oxide (i.e., Adam's catalyst), at a temperature of 20° to 40° C., preferably at or about room temperature, at an initial pressure of approximately 50 p.s.i. in a Parr apparatus until an equivalent quantity of hydrogen has been consumed to give, after removal of the catalyst by filtration and subsequent evaporation of the solvent, the product 2,2-dioxo-3,4-dihydro-1,2,3-benzoxathiazine of Formula V.

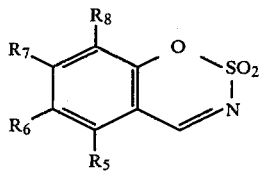

The examples which follow illustrate the substituted 2,2-dioxo-1,2,3-benzoxathiazines and their 3,4-dihydro derivatives of the present invention and the methods by which they are prepared.

EXAMPLE 1

Preparation of 2,2-Dioxo-6-(1,1-dimethylethyl)-8-iodo-1,2,3-benzoxathiazine

To a solution of sulfamoyl chloride (13.8 g, 0.12 mole) in anhydrous methylene chloride (75 ml) is added a solution of 3-iodo-5-(1,1-dimethylethyl)salicylaldehyde (6 g., 0.02 mole) and triethylamine (12.1 g, 0.12 mole) in anhydrous methylene chloride (100 ml.) dropwise with stirring at 20° C. Upon completing the addition, the resulting reaction mixture is stirred at 20° C. for 3 days. Removal of the solvent in vacuo leaves a tacky residue which is partitioned between ether and 2 N hydrochloric acid. After separating the phases, the organic phase is washed with water and saturated brime, dried over sodium sulfate and filtered. Evaporation of the filtrate leaves an oily residue (6 g.) which is chromatographed on silica gel (300 g.) with benzene. Elution with benzene (840 ml.) gives recovered 3-iodo-5-(1,1-dimethylethyl)salicylaldehyde (2.2 g., 37% recovery), m.p. 76°–78° C. Continued elution with benzene (500 ml.) provides an impure solid (2.4 g.) which is triturated with hexane (20 ml.) and filtered to afford the title compound as a pale yellow solid (1.0 g, 14%), m.p. 130°–134° C. Crystallization from hexane benzene (9.1; v:v) gives an analytical sample of 2,2-dioxo-6-(1,1-dimethylethyl)-8-iodo-1,2,3-benzoxathiazine, m.p. 135°–136° C.

Elemental analysis for $C_{11}H_{12}INO_3S$: Calc.: C, 36.18; H, 3.31; N, 3:84. Found: C, 36.14; H, 3.27; N, 3.71.

EXAMPLE 2

Preparation of 2,2-Dioxo-6-(1,1-dimethylethyl)-8-chloro-1,2,3-benzoxathiazine

This compound is prepared by essentially the same procedure as described in Example 1 except that the 3-iodo-5-(1,1-dimethylethyl)salicylaldehyde is replaced by 3-chloro-5-(1,1-dimethylethyl)salicylaldehyde. The following reagents are employed:

3-chloro-5-(1,1-dimethylethyl)salicylaldehyde: 4 g., 0.02 mole
sulfamoyl chloride: 13.8 g., 0.12 mole
triethylamine: 12.1 g., 0.12 mole
anhydrous methylene chloride: 175 ml.
silca gel: 300 g.
benzene: 1.44 l.

The impure product (2.3 g.) eluted from the silica gel column is purified by trituration with hexane (20 ml.). The insoluble solid is collected to give 1.3 g. (24%) of the title compound, m.p. 127°–130° C. Recrystallization from hexane benzene (5:1; v:v) affords analytically pure 2,2-dioxo-6-(1,1-dimethylethyl)-8-chloro-1,2,3-benzoxathiazine as pale yellow crystals, m.p. 130°–131° C.

Elemental analysis for $C_{11}H_{12}ClNO_3S$: Calc.: C, 48.27; H, 4.42; N, 5.12. Found: C, 48.37; H, 4.60; N, 5.18.

EXAMPLE 3

Preparation of 2,2-Dioxo-1,2,3-benzoxathiazine

This compound is prepared by essentially the same method as described in Example 1 except that the 3-iodo-5-(1,1-dimethylethyl)salicylaldehyde is replaced by salicylaldehyde and chloroform rather than benzene is used as the eluant. The following reagents are employed:

salicylaldehyde: 4.88 g., 0.04 mole
sulfamoyl chloride: 27.6 g., 0.24 mole
triethylamine: 24.2 g., 0.24 mole
anhydrous methylene chloride: 300 ml.
silica gel: 300 g.
chloroform: 1.6 l.

Recrystallization of the impure product (4.2 g., 57%), m.p. 44°–47° C., eluted from the silica gel column, from n-butyl chloride provides analytically pure 2,2-dioxo-1,2,3-benzoxathiazine, m.p. 72°–73° C.

Elemental analysis for $C_7H_5NO_3S$: Cal.: c, 45.90; H, 2.75; N, 7.65. Found: C, 45.79; H, 2.87; N, 7.61.

EXAMPLE 4

Preparation of 2,2-Dioxo-6-(1,1-dimethylethyl)-8-trifluoromethyl-1,2,3-benzoxathiazine This compound is prepared by essentially the same procedure as described in Example 1 except that the 3-iodo-5-(1,1-dimethylethyl)salicylaldehyde is replaced by 3-trifluoromethyl-5-(1,1-dimethylethyl)salicylaldehyde. Thereby is obtained 2,2-dioxo-6-(1,1-dimethylethyl)-8-trifluoromethyl-1,2,3-benzoxathiazine.

EXAMPLE 5

Preparation of 2,2-Dioxo-5,7-dimethoxy-6,8-dichloro-1,2,3-benzoxathiazine

This compound is prepared by essentially the same procedure as described in Example 1 except that the 3-iodo-5-(1,1-dimethylethyl)salicylaldehyde is replaced by 3,5-dichloro-4,6-dimethoxysalicylaldehyde. Thereby is obtained 2,2-dioxo-5,7-dimethoxy-6,8-dichloro-1,2,3-benzoxathiazine.

EXAMPLE 6

Preparation of 2,2-Dioxo-6-(1,1-dimethylethyl)-8-methylthio-1,2,3-benzoxathiazine This compound is prepared by essentially the same procedure as described in Example 1 except that the 3-iodo-5-(1,1-dimethylethyl) salicylaldehyde is replaced by 3-methylthio-5-(1,1-dimethylethyl) salicylaldehyde. Thereby is obtained 2,2-dioxo-6-(1,1-dimethylethyl)-8-methyl thio-1,2,3-benzoxathiazine.

EXAMPLE 7

Preparation of 2,2-Dioxo-6-(1,1-dimethylethyl)-8-bromo-1,2,3-benzoxathiazine

The compound is prepared by essentially the same procedure as described in Example 1 except that the 3-iodo-5-(1,1-dimethylethyl)salicylaldehyde is replaced by 3-bromo-5-(1,1-dimethylethyl)salicylaldehyde. Thereby is obtained 2,2-dioxo-6-(1,1-dimethylethyl)-8-bromo-1,2,3-benzoxathiazine.

EXAMPLE 8

Preparation of 2,2-Dioxo-3,4-dihydro-6-(1,1-dimethylethyl)-8-iodo-1,2,3-benzoxathiazine To a solution of 2,2-dioxo-6-(1,1-dimethylethyl)-8-iodo-1,2,3-benzoxathiazine (2 g., 5.5 millimole) in methanol (75 ml.) is added sodium borohydride (0.21 g., 5.5 millimole) portionwise with stirring at 20° C. The resulting reaction solution is stirred at 20° C. for 16 hours and then concentrated in vacuo leaving a residual solid which is triturated with water (50 ml.). The insoluble solid is collected and crystallized from 40% ethanol-acetic acid (25:2, v:v) to give 2,2-dioxo-3,4-dihydro-6-(1,1-dimethylethyl)-8-iodo-1,2,3-benzoxathiazine as colorless crystals (1.7 g., 85%), m.p. 154°–155° C.

Elemental analysis for $C_{11}H_{14}INO_3S$: Calc.: C, 35.98; H, 3.84; N, 3.81. Found: C, 35.98; H, 4.02; N, 3.88.

EXAMPLE 9

Preparation of 2,2-Dioxo-3,4-dihydro-6-(1,1-dimethylethyl)-S-chloro-1,2,3-benzoxathiazine A solution of 2,2-dioxo-6-(1,1-dimethylethyl)-8-chloro-1,2,3-benzoxathiazine (2.5 g., 9.2 millimole) in acetic acid (200 ml.) contained in a Parr apparatus is hydrogenated in the presence of platinum (IV) oxide at 20° C. and a pressure (initial) of 50 p.s.i. for five minutes. The catalyst is removed by filtration and the filtrate is evaporated in vocuo to provide the title compound as a residual solid (2.35 g., 93%), m.p. 158°–160° C. Crystallization from 50% ethanol gives analytically pure 2,2-dioxo-3,4-dihydro-6-(1,1-dimethylethyl)-8-chloro-1,2,3-benzoxathiazine as colorless crystals, m.p. 162°–163° C.

Elemental analysis for $C_{11}H_{14}ClNO_3S$: Calc.: C, 47.91; H, 5.12; N, 5.08. Found: C, 47.76; H, 4.83; N, 5.08.

EXAMPLE 10

Preparation of 2,2-Dioxo-3,4-dihydro-1,2,3-benzoxathiazine

This compound is prepared by essentially the same method as described in Example 9 except that the 2,2-dioxo-6-(1,1-dimethylethyl)-8-chloro-1,2,3-benzoxathiazine is replaced by 2,2-dioxo-1,2,3-benzoxathiazine. The following reagents are employed:

2,2-dioxo-1,2,3-benzoxathiazine: 2.6 g., 0.014 mole
acetic acid: 200 ml.
platinum (IV) oxide: 100 mg (catalyst)
hydrogen: 5.7 lbs.

Crystallation of the crude hydrogenation product from benzene yields the title compound as colorless crystals (2 g., 77%), m.p. 89°–90° C. Recrystallization from 40% ethanol affords analytically pure 2,2-dioxo-3,4-dihydro-1,2,3-benzoxathiazine, m.p. 89°–90° C.

Elemental analysis for $C_7H_7NO_3S$: Cal.: C, 45.40; H, 3.81; N, 7.56. Found: C, 45.31; H, 3.98; N, 7.56.

EXAMPLE 11

Preparation of 2,2-Dioxo-3,4-dihydro-6-(1,1-dimethylethyl)-8-trifluoromethyl-1,2,3-benzoxathiazine This compound is prepared by essentially the same method as described in Example 8 except that the 2,2-dioxo-6-(1,1-dimethylethyl)-8-iodo-1,2,3-benzoxathiazine is replaced by 2,2-dioxo-6-(1,1-dimethylethyl)-8-trifluoromethyl-1,2,3-benzoxathiazine. Thereby is obtained 2,2-dioxo-3,4-dihydro-6-(1,1-dimethylethyl)-8-trifluoromethyl-1,2,3-benzoxathiazine.

EXAMPLE 12

Preparation of 2,2-Dioxo-3,4-dihydro-5,7-dimethoxy-6,8-dichloro-1,2,3-benzoxathiazine This compound is prepared by essentially the same method as described in Example 8 except that the 2,2-dioxo-6-(1,1-dimethylethyl)-8-iodo-1,2,3-benzoxathiazine is replaced by 2,2-dioxo-5,7-dimethoxy-6,8-dichloro-1,2,3-benzoxathiazine. Thereby is obtained 2,2-dioxo-3,4-dihydro-5,7-dimethoxy-6,8-dichloro-1,2,3-benzoxathiazine.

EXAMPLE 13

Preparation of 2,2-Dioxo-3,4-dihydro-6-(1,1-dimethylethyl)-8-methylthio-1,2,3-benzoxathiazine This compound is prepared by essentially the same method as described in Example 8 except that the 2,2-dioxo-6-(1,1-dimethylethyl)-8-iodo-1,2,3-benzoxathiazine is replaced by 2,2-dioxo-6-(1,1-dimethylethyl)-8-methylthio-1,2,3-benzoxathiazine. Thereby is obtained 2,2-dioxo-3,4-dihydro-6-(1,1-dimethylethyl)-8-methylthio-1,2,3-benzoxathiazine.

EXAMPLE 14

Preparation of 2,2-Dioxo-3,4-dihydro-6-(1,1-dimethylethyl)-8-bromo-1,2,3-benzoxathiazine This compound is prepared by essentially the same method as described in Example 8 except that the 2,2-dioxo-6-(1,1-dimethylethyl)-8-iodo-1,2,3-benzoxathiazine is replaced by 2,2-dioxo-6-(1,1-dimethylethyl)-8-bromo-1,2,3-benzoxathiazine. Thereby is obtained 2,2-dioxo-3,4-dihydro-6-(1,1-dimethylethyl)-8-bromo-1,2,3-benzoxathiazine.

What is claimed is:

1. A method of treating a condition exhibiting at least one of the symptoms of pain, fever and inflammation, which comprises the administration to a patient in need of such treatment a therapeutically effective amount of a compound of the formula:

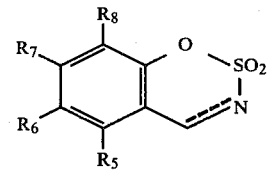

$R_5$ is hydrogen; $C_{1-3}$ alkyl; halogen; or $C_{1-3}$ alkoxy;

$R_6$ is hydrogen; $C_{1-5}$ straight or branched chain alky; or halogen;

$R_7$ is hydrogen; $C_{1-5}$ alkyl; $C_{1-5}$ alkoxy; or halogen;

$R_8$ is hydrogen; halogen; trifluoromethyl; or $C_{1-3}$ alkythio; and the dashed line between the 3- and 4- positions describes alternative saturation or unsaturation.

2. The method of claim 1 wherein for the administered compound, $R_5$ is hydrogen, or $C_{1-3}$ alkoxy;

$R_6$ is hydrogen, halogen, or $C_{3-5}$ branched chain alkyl;

$R_7$ is hydrogen or $C_{1-3}$ alkoxy; and $R_8$ is hydrogen, halogen, trifluoromethyl or $C_{1-3}$ alkylthio.

3. The method of claim 1 wherein for the administered compound, $R_5$ and $R_7$ are hydrogen or methoxy;

$R_6$ is hydrogen, chloro, bromo, iodo, or $C_{3-5}$ branched chain alkyl; and $R_8$ is hydrogen, cloro, bromo, iodo, trifluoromethyl or methylthio.

4. The method of claim 1 wherein the administered compound is 2,2-dioxo-6-(1,1-dimethylethyl)-8-chloro-1,2,3-benzoxathiazine.

5. The method of claim 1 wherein the administered compound is 2,2-dioxo-3,4-dihydro-6-(1,1-dimethylethyl)-8-chloro-1,2,3-benzoxathiazine.

6. A pharmaceutical composition comprising an anti-inflammatory, anti-pyretic, or analgesic effective amount of a compound of the formula:

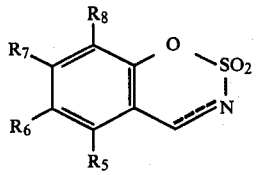

wherein
$R_5$ is hydrogen; $C_{1-3}$ alkyl; halogen; or $C_{1-3}$ alkoxy;
$R_6$ is hydrogen; $C_{1-5}$ straight or branched chain alkyl; or halogen;
$R_7$ is hydrogen; $C_{1-5}$ alkyl; $C_{1-5}$ alkoxy; or halogen;
$R_8$ is hydrogen; halogen; trifluoromethyl; or $C_{1-3}$ alkylthio; and
the dashed line between the 3- and 4- positions describes alternative saturation or unsaturation; in a non-toxic, pharmaceutically acceptable carrier.

7. The composition of claim 6 wherein for the compound,
$R_5$ is hydrogen; or $C_{1-3}$ alkoxy;
$R_6$ is hydrogen, halogen, or $C_{3-5}$ branched chain alkyl;
$R_7$ is hydrogen or $C_{1-3}$ alkoxy; and
$R_8$ is hydrogen, halogen, trifluoromethyl or $C_{1-3}$ alkylthio.

8. The composition of claim 6 wherein for the compound,
$R_5$ and $R_7$ are hydrogen or methoxy;
$R_6$ is hydrogen, chloro, bromo, iodo, or $C_{3-5}$ branched chain alkyl; and
$R_8$ is hydrogen, chloro, bromo, iodo, trifluoromethyl or methylthio.

9. The composition of claim 6 wherein the compound is 2,2-dioxo-6-(1,1-dimethylethyl)-8-chloro-1,2,3-benzoxathiazine.

10. The composition of claim 6 wherein the compound is 2,2-dioxo-3,4-dihydro-6-(1,1-dimethylethyl)-8-chloro-1,2,3-benzoxathiazine.

* * * * *